United States Patent [19]

Wang

[11] Patent Number: 4,954,584

[45] Date of Patent: Sep. 4, 1990

[54] THERMOSETTING RESIN COMPOSITIONS

[75] Inventor: Pen-Chung Wang, Houston, Tex.

[73] Assignee: Shell Oil Company, Houston, Tex.

[21] Appl. No.: 364,276

[22] Filed: Jun. 12, 1989

[51] Int. Cl.$^5$ ............................................. C08G 59/16
[52] U.S. Cl. ..................................... 525/507; 528/99;
528/112; 528/322; 528/361; 528/363
[58] Field of Search ................. 525/507; 528/112, 322,
528/361, 99, 363

[56] References Cited

U.S. PATENT DOCUMENTS

| | | | |
|---|---|---|---|
| 3,696,111 | 10/1972 | Juby et al. ........................ | 560/102 X |
| 4,371,688 | 2/1983 | Moore ................................. | 528/112 |
| 4,451,637 | 5/1984 | Yamato et al. ................. | 528/112 X |
| 4,492,789 | 1/1985 | Nakashima et al. ............ | 528/112 X |
| 4,540,763 | 9/1985 | Kirchhoff ............................ | 526/281 |

Primary Examiner—Earl Nielsen

[57] ABSTRACT

Thermosetting resin compositions comprise a mixture of a 1-arylcyclobutenecarboxylate ester of a glycidyloxy compound having at least two glycidyloxy substituents and at least one polymerizable monomer having at least two substituents with multiple valence bonds between adjacent atoms. Also claimed are the cured products obtained by heating such compositions.

19 Claims, No Drawings

THERMOSETTING RESIN COMPOSITIONS

FIELD OF THE INVENTION

This application relates to resin compositions which cure or crosslink upon application of heat to produce insoluble, crosslinked solids. More particularly, the invention relates to thermosetting resin compositions wherein a first component is an arylcyclobutenecarboxylate) ester of a glycidyloxy compound, mixed with at least one additional polymerizable monomer. The invention also relates to the cured products obtained from the compositions.

BACKGROUND OF THE INVENTION

The curing of monomeric materials to produce thermoset resins is well known in the art. In general, the polymerizable monomers have at least one and customarily more than one reactive group which serves as a site for the curing or crosslinking polymerization to produce the cured insoluble solids which are typically highly crosslinked. There are some polymerizable monomeric materials wherein the active sites are such that the monomer will cure upon application of energy, e.g., heat or high intensity UV light. In many if not most cases, however, a curing agent is necessary to allow the curing or crosslinking reaction to proceed at an acceptable rate. The curing agents are catalytic or are stoichiometric relative to the resin to be crosslinked. The stoichiometric curing agents, i.e., agents which are employed in substantial quantities relative to the quantity of the resin, are the more commonly utilized and are typically multi-functional polymerizable compounds having a plurality of reactive groups capable of participating in crosslinking reactions. A mixture of a thermoset resin and a curing agent is then cured by application of heat, with or without the presence of an accelerator added to obtain a more acceptable curing rate.

Thermoset resins containg arylcyclobutene moieties, especially benzocyclobutene moieties, are known in the art. A series of U.S. Patents to Kirchhoff, illustrated by U.S. Pat. No. 4,540,763, describes the production and curing of a large number of benzocyclobutene derivatives wherein the benzocyclobutene moieties are connected by linking groups substituted on a carbon atom of a six-membered ring of the arylcyclobutene ring system. A copending U.S. patent application Ser. No. 364,275, filed June 12, 1989, describes and claims a class of arylcyclobutenecarboxylate esters wherein the ester group which serves to connect the arylcyclobutene moiety to the remainder of the molecule is substituted on a carbon atom of a four-membered ring of the aryclocyclobutene ring system. Also claimed are the self-cured products obtained therefrom.

It would be of advantage to provide a novel class of thermosetting resin compositions which cure at an acceptable rate without the requirement for accelerators to produce highly crosslinked, insoluble solids having good properties of strength and rigidity.

SUMMARY OF THE INVENTION

This invention relates to curable thermosetting resin compositions comprising a 1-arylcyclobutenecarboxylate) ester compound and at least one additional polymerizable monomer compound of different chemical structure. More particularly, the invention relates to such compositions wherein the additional polymerizable monomer(s) have at least two substituents with multiple bonds between adjacent atoms. The invention also relates to the cured products which are obtained by heating the thermosetting resin compositions.

DESCRIPTION OF THE INVENTION

The resin compositions of the invention comprise a mixture of an arycyclobutenecarboxylate ester compound with at least one additional polymerizable monomeric compound. The arylcyclobutenecarboxylate ester compound has at least two 1-arylcyclobutene moieties connected through the ester group of the 1-arylcyclobutenecarboxylate to an organic linking group which forms the rest of the resin molecule. A wide variety of 1-arylcyclobutenecarboxylate compounds are useful in the compositions of the invention because of the presence therein of a plurality of the arylcyclobutenecarboxylate groups. The preferred 1-arylcyclobutenecarboxylate derivatives, however, are ester derivatives of an aromatic glycidyloxy compound. Without wishing to be bound by any particular theory, the esters are illustratively produced by reaction of the carboxyl group of the 1-arylcyclobutenecarboxylic acid and the glycidyl groups of the glycidyloxy compound to open each glycidyl ring and produce an ester linkage between the arylcyclobutene moiety and the terminal or gamma carbon atom of the former glycidyloxy substituent as well as a hydroxyl group at the 2-position.

The 1-arylcyclobutenecarboxylic acid is a compound of the formula $A-CO_2H$ wherein A is an arylcyclobutene ring system with the carboxyl group substituted at the 1-position. The arylcyclobutene ring system A is an aromatic ring system of up to 4 aromatic rings and up to 30 carbon atoms, inclusive, which contains at least one cyclobutene ring fused to an aromatic ring. Suitable aromatic ring systems are represented by the single aromatic ring compound benzene, the fused ring compounds such as naphthalene, anthracene and phenanthrene, the directly-connected ring system compounds such as biphenyl and 1-phenylnaphthalene or the alkylene-connected ring systems of two or more rings connected by an alkylene group, e.g., the diphenylalkanes including diphenylmethane and 2,2-diphenylpropane. The preferred ring system is a single ring and the preferred arylcyclobutene moiety is a benzocyclobutene moiety. The arylcyclobutene ring system is hydrocarbyl and as otherwise unsubstituted except for the carboxyl group and most preferred as the arylcyclobutenecarboxylic acid is 1-benzocyclobutenecarboxylic acid.

The 1-arylcyclobutenecarboxylic acids are known or are produced by known methods. A general view of arylcyclobutene chemistry particularly benzocyclobutene chemistry, is provided by Klundt, Chemical Reviews, Vol. 70, No. 4 pp. 471–487 (1970) and by other references provided by the review article. By way of a specific preparative example, 1-benzocyclobutenecarboxylic acid is produced by rearrangement of an α-diazandanone.

The glycidyloxy compounds of the invention are compounds, whether monomeric or polymeric, which are characterized by the presence within the molecular structure of at least two glycidyloxy groups, i.e., substituents.

The glycidyloxy compounds are aromatic including a mixture of aromatic and aliphatic moieties and are otherwise hydrocarbyl except for the oxygen atoms of the glycidyloxy groups or are substituted hydrocarbyl containing additional atoms in the form of inert carbon atom substituents, e.g., halogen atoms, preferably the middle halogens chloro or bromo, or in the form of inert divalent linking groups connecting portions of the molecule.

The monomeric glycidyloxy compounds have up to 30 carbon atoms and up to 3 aromatic rings, inclusive, and from 2 to 4 glycidyloxy substituents. A preferred class of monomeric glycidyloxy compounds is represented by the formula $$G_g—R—(X—R)_r G_g \quad (I)$$

wherein R independently is aromatic of up to 15 carbon atoms and up to 2 aromatic rings, inclusive, X is a direct valence bond, alkylene of up to 20 carbon atoms inclusive, oxo, thio, sulfonyl, carbonyl, oxyphenylene, i.e.,

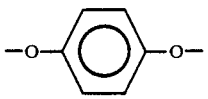

w,w-di(oxyphenyl)propane, i.e.,

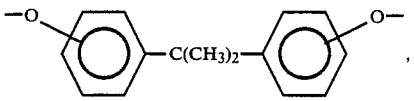

or dioxydiphenylene, i.e.,

G is glycidyloxy, g independently is 1 or 2 and r is 0 or 1. Preferred R groups have up to 10 carbon atoms, have one aromatic ring and are hydrocarbyl. Particularly preferred R groups are phenylene, especially p-phenylene, and glycidyloxy compounds which are glycidyloxyphenyl compounds.

Illustrative of such monomeric glycidyloxy compounds are 1,4diglycidyloxybenzene, 1,3,5-triglycidyloxybenzene, 1,4-di(glycidyloxy)naphthalene, di(4-glycidyloxyphenyl)ether, 2,2-di(4-glycidyloxyphenyl)propane, di(3-glycidyloxy-4-methylphenyl)ketone, ei(4-glycidyloxyphenyl)methane, 4,4'-diglycidyloxybiphenyl, 1-[4,5-di(glycidyloxy)naphthyl]4-glycidyloxyphenyl sulfone, 3,3', 5-triglycidyloxybiphenyl and di(4-glycidyloxy-2-chlorophenyl)methane.

In general, compounds of the above formula I are preferred wherein each of g and r are 1 and X is alkylene, oxo, sulfonyl or carbonyl. Particularly preferred are the di(glycidyloxyphenyl)alkanes, i.e., X is alkylene, preferably alkylene of up to 8 carbon atoms, especially 2,2-di(4-glycidyloxyphenyl)propane.

The monomeric glycidyloxy compounds are known compounds or are produced by known methods. For example, a glycidyloxy compound is produced from the corresponding hydroxy compound by reaction with a stoichiometric quantity of epichlorohydrin and a base, particularly an alkali metal base. Certain of the glycidyloxy compounds, particularly 2,2-di(4-glycidyloxyphenyl)propane are commercial products used in the production of certain epoxy resins.

The polymeric glycidyloxy compounds which are useful as precursors of the ester component of the compositions of the invention are oligomers, i.e., low molecular weight polymers, having moieties derived from an epihalohydrin and a hydroxyphenylalkane. In one modification, the oligomer is produced by reaction of a molar excess of an epihalohydrin such as epichlorohydrin and a di(hydroxyphenyl)alkane to prepare glycidyl ethers of hydroxyphenylalkane moieties joined by hydroxypropane ether or by other groups. Such oligomers exist in a number of structural types but are well known in the arts. In one class of such oligomers, the oligomer is an alternating oligomer characterized by alternating di(oxyphenyl)alkane and 2-hydroxy-1,3-propylene moieties and is capped with glycidyl groups, for example, the oligomers of the formula

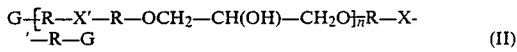

wherein G and R have the previously stated meanings and X' is alkylene of up to 20 carbon atoms, inclusive. The term n is an integer from 1 to about 40, preferably from 1 to about 20. It will be appreciated that within a given oligomer sample there will be oligomer molecules which have differing values for n so that, on average, n is not necessarily a whole number. A particularly preferred class of the oligomers of formula 11 are those produced from epichlorohydrin and 2,2-di(4-hydroxyphenyl)propane. Such oligomers are depicted by the above formula II wherein each R is p-phenylene and each X' is 2,2-propylene.

The production of these oligomers is conventional and well known in the art and is illustrated by the disclosures of Locatelli, U.S. Pat. No. 4,269,952, Alber et al., U.S. Pat. No. 4,036,054, and Wang et al., U.S. Pat. No. 4,499,255. A number of the oligomers are commercial and are marketed by Shell Chemical Company under the trademark EPON® Epoxy Resins.

In an alternate although generally less preferred embodiment of the polymeric glycidyloxy compounds, the oligomers are polyglycidyloxy ethers of a poly(hydroxyphenylalkane). These oligomers are represented by the glycidyl ethers of the poly(hydroxyphenylalkanes) commonly referred to as Novolac resins. The glycidyl derivatives of such resins are illustrated by the formula

wherein G, R, X' and n have the previously stated meanings. A preferred class of such derivatives of these Novolac resins are those of the above formula III wherein R is o-phenylene and X' is methylene.

The Novolac-type resins are produced by conventional procedures from a phenol and an aldehyde, frequently formaldehyde, or a cyclic diene, for example, dicyclopentadiene. The disclosure of Speranza, U.S. Pat. No. 4,102,866, is illustrative. The glycidyl ethers are produced from the resins by the methods described above.

To produce the arylcyclobutenecarboxylate esters, the 1-arylcyclobutenecarboxylic acid and the glycidyloxy compound are preferably employed in substantially stoichiometric quantities, that is, about 1 mole of arylcyclobutenecarboxylic acid for each mole of glycidyloxy group present in one mole of the glycidyloxy compound. However, reactant ratios of moles of arylcyclobutenecarboxylic acid to moles of glycidyloxy group from about 4:1 to about 1:2 are satisfactory.

The esterification reaction is conducted in the substantial absence of reaction diluent when the reactants are liquid at reaction conditions or in the presence of an inert reaction diluent such as toluene when one or both of the reactants are solid at reaction temperature. A satisfactory reaction rate is most easily obtained if a catalyst is employed when the 1-arylcyclobutenecarboxylic acid and the glycidyloxy compound are contacted. Quaternary phosphonium halides and quaternary ammonium halides have been found to be useful as the catalyst, particularly tetra(hydrocarbyl)phosphonium halides wherein at least one of the hydrocarbyl substituents is phenyl with any other substituents being alkyl, particularly lower alkyl, and the halide is a middle halide, i.e., chloride or bromide. Illustrative of such phosphonium halides are trimethylphenylphosphonium chloride, ethyltriphenylphosphoniums bromide, di-n-butyldiphenylphosphonium bromide and tetraphenylphosphonium chloride. Alkyltriphenylphosphonium halides are preferred, especially ethyltriphenylphosphonium bromide. The phosphonium halide is employed in a catalytic quantity. Amounts of phosphonium halide from about 1% by weight to about 10% by weight, based on total reactants, are satisfactory with amounts from about 2% by weight to about 6% by weight on the same basis being preferred.

The reaction is conducted by intimately contacting the acid reactant, the glycidyloxy compound reactant, the catalyst and any diluent to be employed and maintaining the mixture under reaction conditions. An elevated reaction temperature is generally utilized and reaction temperature from about 30° C. to about 200° C. are satisfctory with reaction temperatures from about 50° C. to about 150° C. being preferred. The reaction pressure to be employed is a pressure which is sufficient to maintain the reaction mixture in a liquid phase. Such pressures are typically up to about 10 atmospheres but more often are from about 0.8 atmospheres to about 5 atmospheres.

Subsequent to reaction, the arylcyclobutenecarboxylate ester is obtained from the product mixture. If desired, the ester product is separated and purified by conventional methods such as selective extraction, precipitation or solvent removal. Particularly in the embodiment where the reactents are employed in substantially stoichiometric ratios without the utilization of added diluent, the product is obtained in sufficiently high conversion and selectivity so as to allow its use in most applications without the need for purification.

The ester products are 1-arylcyclobutenecarboxylate esters of the glycidyloxy compound illustratively produced by opening of the glycidyl rings with the formation of an ester linkage on the terminal carbon atom of the former glycidyl groups and the formation of a hydroxyl substituent on the center carbon atom. In terms of the monomeric reactants of formula I as described above, the ester products are illustrated by the formula

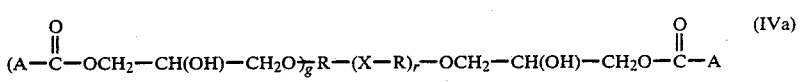

wherein A, R, X, g and r have the previously stated meanings. In terms of the polymeric glycidyloxy compounds of formulas II and III, the products are illustrated by the formula

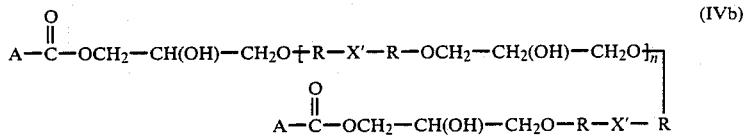

or by the formula

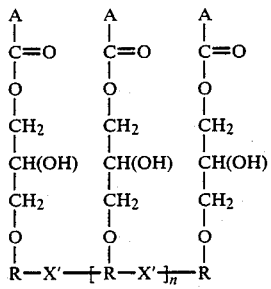

respectively, where A, R, X' and n have the previously stated meanings. The nomenclature of the products, particularly the polymeric products, is difficult because of the complexity thereof. By way of specific illustration, however, the product of 1-benzenecyclobutenecarboxylic acid and 2,2-di(4-hydroxyphenyl)-propane is 2,2-di[4-(3-oxy-2-hydroxypropyloxy)-phenyl]propane di(1-benzocyclobutenecarboxylate). The identity of other products will be apparent from consideration of the above formula for the reactants and the products.

The remaining portion of the thermosetting resin compositions of the invention comprises at least one additional polymerizable monomer having at least two substituents with multiple bonds, i.e., more than a single bond, between adjacent atoms. Although the precise nature of the interaction between the ester products and the additional polymerizable monomer(s) is not known with certainty, it is considered likely that at least in certain instances the cyclobutene portions of the ester products react with the multiple bonds of the additional polymerizable monomer, perhaps to form products of the Diels-Alder type. By whatever mechanism the reaction takes place, the additional polymerizable monomers which are useful in the compositions of the invention have substituents within the molecule with multiple bonds between adjacent atoms and at least two of such substituents in order to permit crosslinking of the compositions.

Polymerizable monomers having a variety of substituents are useful in the compositions of the invention provided that the polymerizable monomer has at least two functional moieties in the molecule having multiple bonds between adjacent atoms. The substituents are hydrocarbyl with the multiple bonds occurring between adjacent carbon atoms or are non-hydrocarbyl with multiple bonds occurring between one carbon atoms and a non-carbon atom or between two atoms, neither of which is carbon. Preferred among such substituents, however, are hydrocarbon substituents such as allyl, propargyl and styrylmethyl and non-hydrocarbon substituents such as cyanato and maleimido.

The structure of the remainder of the molecule to which the multiple bonded substituents are attached is not critical provided that it is inert under the conditions at which the compositions of the invention are cured and are not unduly sterically hindered, and a variety of organic linking groups which meet these criteria are suitably found in the additional polymerizable monomers. In the preferred embodiments of the invention, the moieties which link the reactive substituents together are the group L, where L is 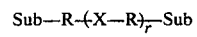 in which R, X and r have the previously stated meanings, or the isocyanurate group, i.e., the

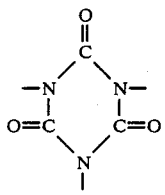

group, with the proviso that when the substituent linking group is isocyanurate, the substituents are allyl.

In the embodiments of the invention where the additional polymerizable monomer incorporates an L linking group, the additional polymerizable monomer is represented by the formula Sub—L—Sub wherein Sub is a substituent selected from the allyl, proparyl, styrylmethyl, cyanato or maleimido, L has the previously stated meaning. The additional polymerizable monomers are further represented by the formula

wherein Sub, R, X and r have the previously stated meanings.

Illustrative of such additional polymerizable monomers are 1,9decadiene, diallyl ether, di(3-cyanatophenyl)methane, 1,5-dicyanatonaphthalene, 1,4-di(maleimido)biphenyl, 1,3-dipropargylbenzene, bis(4-maleimidophenyl) sulfone, 1-allyl-4-styrylmethylbenzene, 2,3-di(4-cyanatophenyl)propane, di(4-maleimidophenyl)methane and divinylbenzene.

in the embodiment where the linking group is isocyanurate and the substituent group is allyl, the additional polymerizable monomer is triallylisocyanurate.

The compositions of the invention comprise the 1-arylcyclobutenecarboxylate ester and at least one additional polymerizable monomer. The compositions usefully comprise the ester plus one or two or even more additional polymerizable monomers as above defined but preferably the compositions comprise the ester and from one to two additional polymerizable monomers. The precise proportions of the compositions of the invention are not critical and each component is suitably present in a quantity from about 1% by weight to about 99% by weight based on total composition. In preferred embodiments of the invention, the 1-arylcyclobutenecarboxylate ester is present in a quantity of at least about 40% by weight on the same basis with the additional polymerizable monomer(s) being present in a total of no more than about 60% be weight. In more preferred embodiments, the 1-arylcyclobenzenecarboxylate ester is present in a quantity of at least about 50% by weight, based on total composition, a first additional polymerizable monomer is present in a quantity of at least about 40% by weight with any other additional polymerizable monomer being present as the remainder of the composition.

The compositions of the invention are produced by forming an intimate mixture of the 1-arylcyclobutenecarboxylate ester and the additional polymerizable monomer. The method of mixing is not critical and conventional methods of co-melting, stirring or blending are satisfactory provided that the mixing does not result in sufficient heat or energy to cause the cure of the compositions.

The compositions of the invention are cured or crosslinked by application of heat. Curing or crosslinking is usually conducted by heating the composition to a curing temperature of at least 150° C. and preferably to a temperature from about 175° C. to about 300° C. It is often desirable to effect the curing by heating in two states. Initially the composition is maintained at a relatively low curing temperature, e.g., from about 175° C. to about 210° C., for a time sufficient to initiate crosslinking and then maintained at a higher curing temperature to complete the cure. The cured products are highly crosslinked solids having good properties of rigidity and strength. The compositions are processed by methods which are conventional for thermosetting resin compositions and are useful in coating and structural applications in the aerospace and electronic industries.

The invention is further illustrated by the following Illustrative Embodiments which should not be regarded as limiting.

ILLUSTRATIVE EMBODIMENT I

A mixture of 29.6 g (0.2 mole) of 1-benzocyclobutenecarboxylic acid, 34.0 g (0.1 mole) of 2,2-bis(4-glycidyloxyphenyl)propane and 0.3 g of ethyltriphenylphosphonium bromide was stirred at 50° C. for 2 hours and at 100° C. for 12 hours. The resulting product, obtained in greater than 99% yield, was

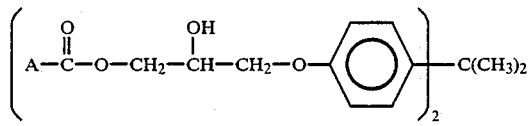

The identity of the product was confirmed by $^{13}$C-NMR analysis which was consistent with the above structure. The ester product is a viscous liquid.

ILLUSTRATIVE EMBODIMENT II

A mixture of equal parts by weight of the ester product of illustrative Embodiment I and bis(4-maleimidophenyl)methane was melted at 100°–120° C. The resulting mixture was heated in an oven at 200° C. for 2 hours and then at 220° C. for an additional 4 hours. The resulting cured product had a glass transition temperature of 191° C.

ILLUSTRATIVE EMBODIMENT III

A mixture of equal parts by weight of the ester of Illustrative Embodiment I and 2,2-bis(4-cyanatophenyl)propane was melted at 100°–120° C. The resulting mixture was heated in an oven at 200° C. for 2 hours and then at 220° C. for an additional 4 hours. The resulting cured material had a glass transition temperature of 112° C.

ILLUSTRATIVE EMBODIMENT IV

A mixture of equal parts by weight of the ester of Illustrative Embodiment I and triallylisocyanurate was melted at 100°–120° C. The resulting mixture was heated in an oven at 200° C. for 2 hours and then at 220° C. for an additional 4 hours. The resulting cured product had a glass transition temperature of 121° C.

ILLUSTRATIVE EMBODIMENT V

A mixture of 50 parts by weight of the ester of Illustrative Embodiment I, 5 parts by weight of bis(4-maleimidophenyl)methane and 45 parts by weight of 2,2-bis(4-cyanatophenyl)propane was heated at 100°–120° C. The resulting mixture was heated in an oven at 200° C. for 2 hours and then at 220° C. for an additional 4 hours. The resulting cured product had a glass transition temperature of 154° C.

What is claimed is:

1. A curable thermosetting resin composition comprising (a) a 1-arylcyclobutenecarboxylic acid ester of a glycidyloxy compound wherein the arylcyclobutene moiety has up to 4 aromatic rings and up to 30 carbon atoms, inclusive, and has at least one cyclobutene ring fused to an aromatic ring, and the glycidyloxy compound has at least two glycidyloxy substituents, and (b) at least one additional polymerizable monomer having at least two functional moieties in the molecule with multiple bonds between adjacent atoms.

2. The composition of claim 1 wherein the 1-arylcyclobutenecarboxylic acid is 1-benzocyclobutenecarboxylic acid and the glycidyloxy compound is represented by the formula $$G_g-R+X-R)_rG_g$$

wherein G is glycicyloxy, R is aromatic of up to 15 carbon atoms and up to 2 aromatic rings, inclusive, X is a direct valence bond, alkylene of up to 8 carbon atoms inclusive, oxo, thio, sulfonyl, carbonyl, dioxyphenylene, 2,2-di(oxyphenyl)propane or dioxydiphenylene, g independently is 1 or 2 and r is 0 or 1.

3. The composition of claim 3 wherein at least one additional polymerizable monomer has at least two substituents selected from allyl, propargyl, styrylmethyl, cyanato or maleimido connected by a linking group selected from —R—(X—R)$_r$— wherein R, X and r have the previously stated meanings or isocyanurate, with the proviso that when the linking group is isocyanurate the substituents are allyl.

4. The composition of claim 3 wherein, in the ester, R is phenylene, X is alkylene, oxo, sulfonyl or carbonyl, G is 1, and r is 1, and in the additional polymerizable monomer the linking group is —R—(X—R)$_r$— in which R is phenylene, X is alkylene, oxo, sulfonyl or carbonyl and r is 1.

5. The composition of claim 4 having from 1 to 2 additional polymerizable monomers.

6. The composition of claim 5 wherein the ester is present in at least about 40% by weight based on total composition.

7. The composition of claim 6 wherein the ester is a di(1-benzocyclobutenecarboxylate)ester of a di(-glydicyloxyphenyl)alkane.

8. The composition of claim 7 wherein the di(-glycicyloxyphenyl)-alkane is 2,2-di(4-glycidyloxyphenyl)propane.

9. The composition of claim 1 wherein the 1-arylcyclobutenecarboxylic acid is 1-benzocyclobutenecarboxylic acid and the glycidyloxy compound is represented by the formula

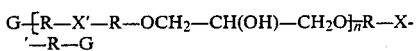

wherein G is glycidyloxy, R is aromatic of up to 15 carbon atoms and up to 2 aromatic rings, inclusive, X' is alkylene of up to 8 carbon atoms inclusive an n is an integer from 1 to about 40.

10. The composition of claim 9 wherein at least one additional polymerizable monomer has at least two substituents selected from allyl, propargyl, styrylmethyl, cyanato or maleimido connected by a linking group selected from (a) —R—(X—R)$_r$—wherein R has the previously stated meaning, X is a direct valence bond, alkylene of up to 8 carbon atoms inclusive, oxo, thio, sulfonyl, carbonyl, dioxyphenylene, 2,2-di(oxyphenyl)-propane or dioxydiphenylene, and r is 0 or 1, or (b) isocyanurate, with the proviso that when the linking group is isocyanurate the substituent is allyl.

11. The composition of claim 10 wherein, within the ester, R is p-phenylene.

12. The composition of claim 11 having from 1 to 2 additional polymerizable monomers.

13. The composition of claim 12 wherein X' is 2,2-propylene.

14. The composition of claim 13 wherein the ester is present in at least 40% by weight based on total composition.

15. The composition of claim 1 wherein the 1-arylcyclobutenecarboylic acid is 1-benzocyclobutenecarboxylic acid and the glycidyloxy compound is represented by the formula

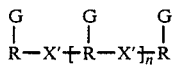

wherein G is glycicyloxy, R is aromatic of up to 15 carbon atoms and up to 2 aromatic rings, inclusive, X' is alkylene of up to 8 carbon atoms inclusive and n is an integer from 1 to about 40.

16. The composition of claim 15 wherein at least one additional polymerizable monomer has at least two substituents selected from allyl, propargyl, styrylmethyl, cyanato or maleimido connected by a linking group selected from (a) —R—(X—R)$_r$— wherein R has the previously stated meaning, X is a direct valence bond, alkylene of up to 8 carbon atoms inclusive, oxo, thio, sulfonyl, carbonyl, dioxyphenylene, 2,2-di(oxyphenyl)propane or dioxydiphenylene, and r is 0 or 1, or (b) isocyanurate, with the proviso that when the linking group is isocyanurate the substituent is allyl.

17. The composition of claim 16 where, within the ester, R is o-phenylene and X' is methylene.

18. The composition of claim 17 having from 1 to 2 additional polymerizable monomers.

19. The composition of claim 18 wherein the ester is present in at least 40% by weight, based on total composition.

* * * * *